United States Patent
Morita et al.

(10) Patent No.: US 6,531,624 B1
(45) Date of Patent: Mar. 11, 2003

(54) AMINOACRYLIC ACID DERIVATIVES AND PROCESS FOR PRODUCING THE SAME

(75) Inventors: Naoto Morita, Osaka (JP); Takashi Inagaki, Osaka (JP)

(73) Assignees: Asahi Glass Company Ltd., Tokyo (JP); Katayama Seiyakusyo Co., Ltd., Hirakata (JP)

( * ) Notice: Subject to any disclaimer, the term of this patent is extended or adjusted under 35 U.S.C. 154(b) by 0 days.

(21) Appl. No.: 09/850,742

(22) PCT Filed: Nov. 17, 1999

(86) PCT No.: PCT/JP99/06422

§ 371 (c)(1),
(2), (4) Date: May 18, 2001

(87) PCT Pub. No.: WO00/29369

PCT Pub. Date: May 25, 2000

(30) Foreign Application Priority Data

Nov. 18, 1998 (JP) ............................................. 10-328450

(51) Int. Cl.$^7$ ...................... C07C 205/00; C07C 229/00
(52) U.S. Cl. ................................. 560/22; 560/8; 560/19; 560/20; 560/23; 514/312
(58) Field of Search ................................. 560/19, 8, 22, 560/20, 23; 514/312

(56) References Cited

U.S. PATENT DOCUMENTS

| 4,699,992 | A |   | 10/1987 | Grohe |
| 5,073,556 | A |   | 12/1991 | Iwata et al. |
| 5,093,515 | A |   | 3/1992  | Kumai et al. |
| 5,182,401 | A | * | 1/1993  | Grohe |
| 5,859,026 | A | * | 1/1999  | Ito et al. |
| 6,133,260 | A | * | 10/2000 | Matzke et al. |
| 6,288,081 | B1| * | 9/2001  | Petersen et al. |

FOREIGN PATENT DOCUMENTS

| EP | 0 176 846 |   | 4/1986 |
| EP | 0 300 311 |   | 1/1989 |
| EP | 0 641 793 |   | 3/1995 |
| EP | 0641793 A1 | * | 8/1995 |
| JP | 64-40460 |   | 2/1989 |
| JP | 8-198819 |   | 8/1996 |
| JP | 08198819 | * | 8/1996 |
| WO | WO 9622688 | * | 8/1996 |

OTHER PUBLICATIONS

International Preliminary Examination Report for PCT/JP99/06422.*
International Search Report for PCT/JP99/06422.*

* cited by examiner

Primary Examiner—Ceila Chang
Assistant Examiner—Hector M Reyes
(74) Attorney, Agent, or Firm—Oblon, Spivak, McClelland, Maier & Neustadt, P.C.

(57) ABSTRACT

A process for producing a benzoylacrylic acid derivative (formula 1) in high yield through a small number of steps and a simple purification step.

The process comprises reacting 2,4,5-trifluoro-3-methyl-6-nitrobenzoyl chloride with a compound (formula 2) to yield an aminoacrylic acid derivative (formula 1) and then reacting the aminoacrylic acid derivative (formula 1) with an amine derivative represented by $R^2$—$NH_2$, wherein $R^2$ is a cycloalkyl group or the like.

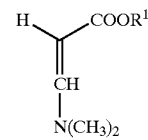

Formula 2

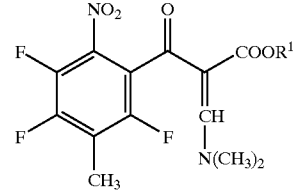

Formula 1

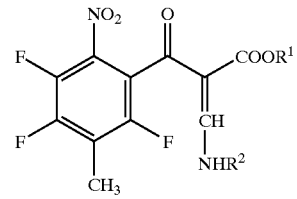

Formula 3

7 Claims, No Drawings

AMINOACRYLIC ACID DERIVATIVES AND PROCESS FOR PRODUCING THE SAME

TECHNICAL FIELD

The present invention relates to a process for producing intermediates of quinolone antibacterial agents and aminoacrylic acid derivatives useful as intermediates of quinolone antibacterial agents.

BACKGROUND ART

Among quinolone compounds having a nitro group at the 5-position, a fluorine atom at the 6-position and a methyl group at the 8-position on the quinolone nucleus, the quinolone compound represented by the following formula 4 and the quinolone compound obtained from the quinolone compound represented by the formula 4 by reductive conversion of the nitro group at the 5-position to an amino group are known. These quinolone compounds are known to have strong antibacterial effect and be useful as synthetic antibacterial agents having reduced phototoxic, clastogenic and convulsive side effects (JP-A-8-198819, EP641793, Chem. Pharm. Bull., 44, 1074–1085(1996)).

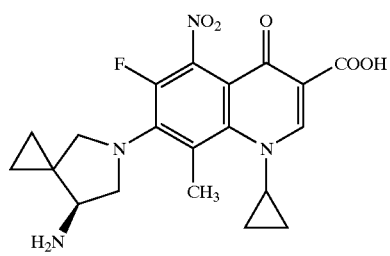

Formula 4

The quinolone intermediate (formula 8) as the starting material for the quinolone compound represented by the formula 4 can be synthesized by the route shown below, namely by reacting 2,4,5-trifluoro-3-methyl-6-nitrobenzoyl chloride with $C_2H_5OMgCH(COOC_2H_5)_2$ to yield the compound (formula 5), hydrolyzing and decarboxlating the compound (formula 5) under heating to yield the compound (formula 6), reacting the compound (formula 6) with an alkyl orthoformate to yield a compound (formula 7: wherein $R^{10}$ is an alkyl group)in the presence of acetic anhydride or propionic anhydride, reacting the compound (formula 7) with cyclopropylamine to yield the compound (formula 3A) and cyclizing the compound (formula 8) (JP-A-8-198819).

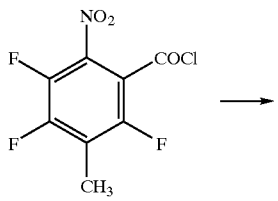

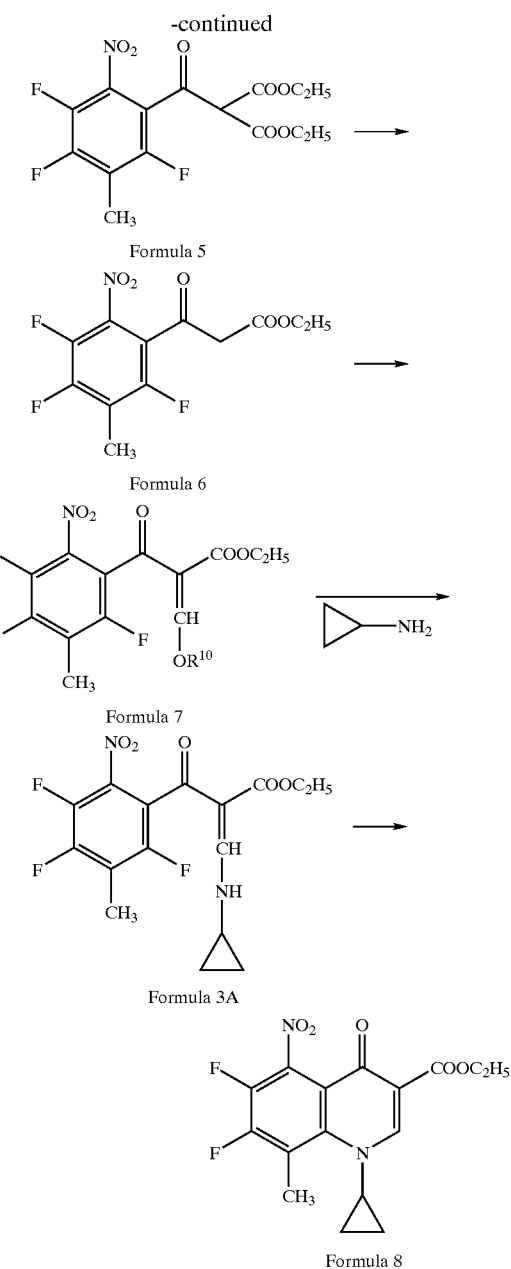

However, the conventional process which requires a number of steps is not efficient and has a problem of low yield.

Further, there is another problem of the formation of the compound represented by the following formula 6A accompanying the formation of the compound (formula 6) which leads to the low yield. Still another problem is inapplicability of recrystallization to purification of the oily compounds (formula 6 and formula 6A). The high boiling points of the compound (formula 6) and the compound (formula 6A) which make it impossible to separate them by distillation are also problematic. For these reasons, in the conventional process, the compound (formula 6A) which remains intact after the formation of compound (formula 7) has been removed by column chromatography.

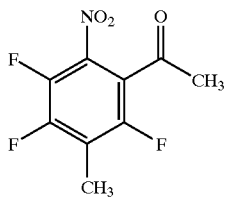

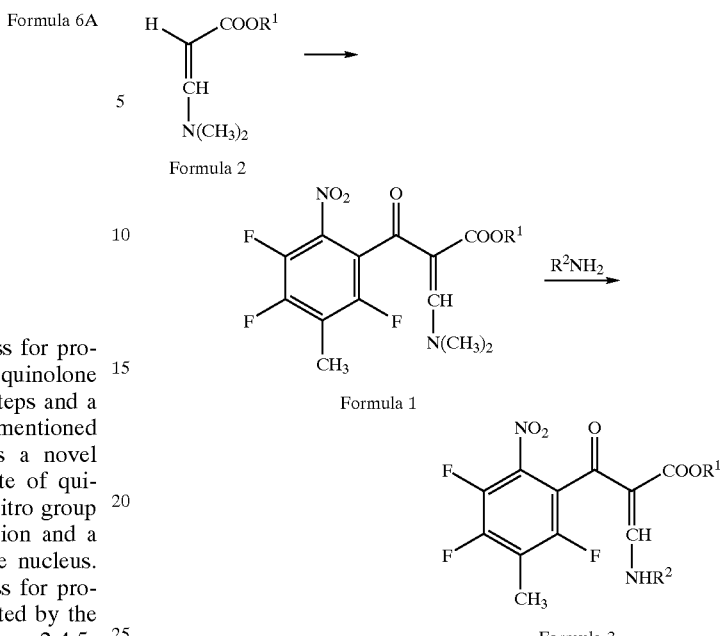

DISCLOSURE OF THE INVENTION

The present invention provides a novel process for producing a highly pure intermediate of synthetic quinolone antibacterial agents through a small number of steps and a simple purification step which solves the above-mentioned problems. The present invention also provides a novel compound (formula 1) useful as an intermediate of quinolone compounds having an amino group or a nitro group at the 5-position, a fluorine atom at the 6-position and a methyl group at the 8-position on the quinolone nucleus. Namely, the present invention provides a process for producing a benzoylacrylic acid derivative represented by the following formula 3, which comprises reacting 2,4,5-trifluoro-3-methyl-6-nitrobenzoyl chloride with a compound represented by the following formula 2 to yield an aminoacrylic acid derivative represented by the following formula 1 and then reacting the aminoacrylic acid derivative represented by the formula 1 with an amine derivative represented by $R^2$—$NH_2$: wherein R is a lower alkyl group, $R^2$ is an alkyl group, a cycloalkyl group, an aralky group, an allyl group, an aryl group, an amino group, an alkylamino group or a dialkylamino group.

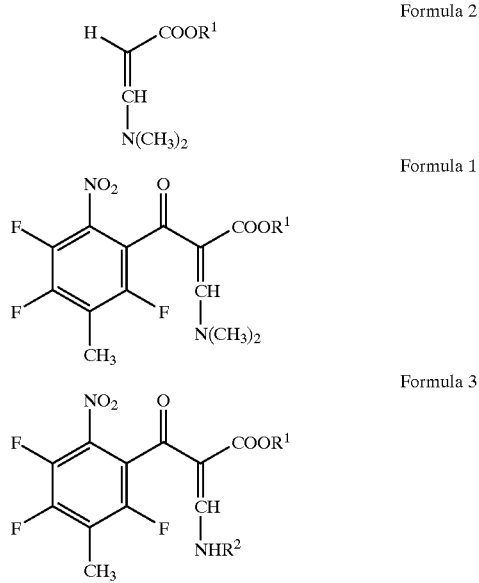

The present invention also provides an aminoacrylic acid derivative represented by formula 1.

BEST MODE FOR CARRYING OUT THE INVENTION

The process of the present invention is represented by the following reaction scheme.

In the process of the present invention, firstly, 2,4,5-trifluoro-3-methyl-6-nitrobenzoyl chloride is reacted with a compound (formula 2) to yield an aminoacrylic acid derivative (formula 1). This reaction step is referred to as reaction step-1 hereinafter.

$R^1$ in formula 2 is a lower alkyl group, preferably a $C_{1-4}$ linear alkyl group, especially preferably a methyl group or an ethyl group. Though the aminoacrylic acid derivative (formula 1) and the compound (formula 2) have cis-isomers and trans-isomers which have substituents at different positions in relation to the double bond, the cis-isomers are preferable in the present invention.

The compound (formula 2) is a known compound and readily obtainable by conventional production processes. Specific examples of the compound (formula 2) include methyl 3-dimethylaminoacrylate, ethyl 3-dimethylaminoacrylate, propyl 3-dimethylaminoacrylate and butyl 3-dimethylaminoacrylate.

In reaction step-1, the amount of the compound (formula 2) is from 0.5 to 10 times, preferably from 1 to 2 times, as many moles as the amount of 2,4,5-trifluoro-3-methyl-6-nitrobenzoyl chloride.

It is preferred to carry out reaction step-1 in the presence of a base.

As the base, a tertiary organic amine represented by $(R^{10})(R^{11})(R^{12})N$ (wherein each of $R^{10}$, $R^{11}$ and $R^{12}$ which may be the same or different, is a $C_{1-4}$ alkyl group or a benzyl group), ammonia, pyridine or a cyclic amine shown below (wherein $R^{13}$, $R^{14}$ $R^{15}$ and $R^{16}$ are independently $C_{1-4}$ alkyl groups or benzyl groups) is preferred.

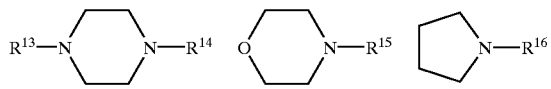

As the base, pyridine is particularly preferred. Use of pyridine as the base reduces production of the by-product and has the advantage of considerable increase in yield.

The amount of the base is from 0.5 to 3 times, preferably from 1 to 2 times, as many moles as the amount of 2,4,5-trifluoro-3-methyl-6-nitrobenzoyl chloride.

It is preferred to carry out reaction step-1 in the presence of a reaction solvent. As the reaction solvent, ethyl acetate, acetonitrile, toluene, xylene, a hydrocarbon solvent, N,N-dimethylformamide or dimethyl sulfoxide may be mentioned. The amount of the reaction solvent is from 1 to 100 times as much by weight as the amount of 2,4,5-trifluoro-3-methyl-6-nitrobenzoyl chloride.

The reaction temperature for reaction step-1 is preferably from 0° C. to 25° C., and the reaction time is preferably from 0.5 to 24 hours. The aminoacrylic acid derivative (formula 1) obtained by this reaction is a novel compound. $R^1$ in formula 1 corresponds to $R^1$ in formula 2 and is the same as defined in formula 2. Specific examples of the aminoacrylic acid derivative (formula 1) include the following compounds:

methyl 3-dimethylamino-2-(2,4,5-trifluoro-3-methyl-6-nitrobenzoyl)acrylate, ethyl 3-dimethylamino-2-(2,4,5-trifluoro-3-methyl-6-nitrobenzoyl)acrylate, propyl 3-dimethylamino-2-(2,4,5-trifluoro-3-methyl-6-nitrobenzoyl)acrylate, and butyl 3-dimethylamino-2-(2,4,5-trifluoro-3-methyl-6-nitrobenzoyl)acrylate.

In the present invention, though the crude reaction product obtained in reaction step-1 may be directly used for reaction step-2 described below, it is preferably subjected to ordinary post-treatment. Especially, when reaction step-1 is carried out in the presence of a base, post-treatment for removal of the resulting salt of the base with hydrochloric acid is preferably carried out before reaction step-2. Because the reaction in reaction step-1 is highly selective and gives a high conversion degree enough to necessitate no special separation operation in the post-treatment, filtration is preferable. The salt of the base with hydrochloric acid is removed sufficiently by filtration. In the present invention, next, the aminoacrylic acid derivative (formula 1) is reacted with an amine derivative represented by $R^2$—$NH_2$ to yield a benzoylacrylic acid derivative (formula 3). This reaction step is referred to as reaction step-2 hereinafter.

$R^2$ in the amine derivative represented by $R^2$—$NH_2$ is an alkyl group, a cycloalkyl group, an aralkyl group, an allyl group, an aryl group, an amino group, a monoalkylamino group or a dialkylamino group. Specific examples of these groups are those shown in the benzoylacrylic acid derivative (formula 3).

As the amine derivative represented by $R^2$—$NH_2$, cyclopropylamine having a cyclopropyl group as $R^2$ is preferable. The amount of the amine derivative represented by $R^2$—$NH_2$ is from 0.5 to 10 times, preferably from 1 to 2 times, as many moles as the amount of the aminoacrylic acid derivative (formula 1).

Examples of the benzoylacrylic acid derivative (formula 3) include the following compounds.

Examples of the benzoylacrylic acid derivative (formula 3) wherein $R^2$ is an alkyl group:

methyl 3-methylamino-2-(2,4,5-trifluoro-3-methyl-6-nitrobenzoyl)acrylate, ethyl 3-methylamino-2-(2,4,5-trifluoro-3-methyl-6-nitrobenzoyl)acrylate, propyl 3-methylamino-2-(2,4,5-trifluoro-3-methyl-6-nitrobenzoyl)acrylate, butyl 3-methylamino-2-(2,4,5-trifluoro-3-methyl-6-nitrobenzoyl)acrylate, methyl 3-ethylamino-2-(2,4,5-trifluoro-3-methyl-6-nitrobenzoyl)acrylate, ethyl 3-ethylamino-2-(2,4,5-trifluoro-3-methyl-6-nitrobenzoyl)acrylate, propyl 3-ethylamino-2-(2,4,5-trifluoro-3-methyl-6-nitrobenzoyl)acrylate, butyl 3-ethylamino-2-(2,4,5-trifluoro-3-methyl-6-nitrobenzoyl)acrylate, methyl 3-propylamino-2-(2,4,5-trifluoro-3-methyl-6-nitrobenzoyl)acrylate, ethyl 3-propylamino-2-(2,4,5-trifluoro-3-methyl-6-nitrobenzoyl)acrylate, propyl 3-propylamino-2-(2,4,5-trifluoro-3-methyl-6-nitrobenzoyl)acrylate, butyl 3-propylamino-2-(2,4,5-trifluoro-3-methyl-6-nitrobenzoyl)acrylate, methyl 3-butylamino-2-(2,4,5-trifluoro-3-methyl-6-nitrobenzoyl)acrylate, ethyl 3-butylamino-2-(2,4,5-trifluoro-3-methyl-6-nitrobenzoyl)acrylate, propyl 3-butylamino-2-(2,4,5-trifluoro-3-methyl-6-nitrobenzoyl)acrylate, and butyl 3-butylamino-2-(2,4,5-trifluoro-3-methyl-6-nitrobenzoyl)acrylate.

Examples of the benzoylacrylic acid derivative (formula 3) wherein $R^2$ is a cycloalkyl group:

methyl 3-cyclopropylamino-2-(2,4,5-trifluoro-3-methyl-6-nitrobenzoyl)acrylate, ethyl 3-cyclopropylamino-2-(2,4,5-trifluoro-3-methyl-6-nitrobenzoyl)acrylate, propyl 3-cyclopropylamino-2-(2,4,5-trifluoro-3-methyl-6-nitrobenzoyl)acrylate, butyl 3-cyclopropylamino-2-(2,4,5-trifluoro-3-methyl-6-nitrobenzoyl)acrylate, methyl 3-cyclobutylamino-2-(2,4,5-trifluoro-3-methyl-6-nitrobenzoyl)acrylate, ethyl 3-cyclobutylamino-2-(2,4,5-trifluoro-3-methyl-6-nitrobenzoyl)acrylate, propyl 3-cyclobutylamino-2-(2,4,5-trifluoro-3-methyl-6-nitrobenzoyl)acrylate, butyl 3-cyclobutylamino-2-(2,4,5-trifluoro-3-methyl-6-nitrobenzoyl)acrylate, methyl 3-cyclopentylamino-2-(2,4,5-trifluoro-3-methyl-6-nitrobenzoyl)acrylate, ethyl 3-cyclopentylamino-2-(2,4,5-trifluoro-3-methyl-6-nitrobenzoyl)acrylate, propyl 3-cyclopentylamino-2-(2,4,5-trifluoro-3-ethyl-6-nitrobenzoyl)acrylate, butyl 3-cyclopentylamino-2-(2,4,5-trifluoro-3-methyl-6-nitrobenzoyl)acrylate, methyl 3-cyclohexylamino-2-(2,4,5-trifluoro-3-methyl-6-nitrobenzoyl)acrylate, ethyl 3-cyclohexylamino-2-(2,4,5-trifluoro-3-methyl-6-nitrobenzoyl)acrylate, propyl 3-cyclohexylamino-2-(2,4,5-trifluoro-3-methyl-6-nitrobenzoyl)acrylate, and butyl 3-cyclohexylamino-2-(2,4,5-trifluoro-3-methyl-6-nitrobenzoyl)acrylate.

Examples of the benzoylacrylic acid derivative (formula 3) wherein $R^2$ is an aralkyl group:

methyl 3-benzylamino-2-(2,4,5-trifluoro-3-methyl-6-nitrobenzoyl)acrylate, ethyl 3-benzylamino-2-(2,4,5-trifluoro-3-methyl-6-nitrobenzoyl)acrylate, propyl 3-benzylamino-2-(2,4,5-trifluoro-3-methyl-6-nitrobenzoyl)acrylate, and butyl 3-benzylamino-2-(2,4,5-trifluoro-3-methyl-6-nitrobenzoyl)acrylate.

Examples of the benzoylacrylic acid derivative (formula 3) wherein $R^2$ is an allyl group:

methyl 3-allylamino-2-(2,4,5-trifluoro-3-methyl-6-nitrobenzoyl)acrylate, ethyl 3-allylamino-2-(2,4,5-trifluoro-3-methyl-6-nitrobenzoyl)acrylate, propyl 3-allylamino-2-(2,4,5-trifluoro-3-methyl-6-nitrobenzoyl)acrylate, and butyl 3-allylamino-2-(2,4,5-trifluoro-3-methyl-6-nitrobenzoyl)acrylate.

Examples of the benzoylacrylic acid derivative (formula 3) wherein $R^2$ is an aryl group:

methyl 3-anilino-2-(2,4,5-trifluoro-3-methyl-6-nitrobenzoyl)acrylate, ethyl 3-anilino-2-(2,4,5-trifluoro-3-methyl-6-nitrobenzoyl)acrylate, propyl 3-anilino-2-(2,4,5-trifluoro-3-methyl-6-nitrobenzoyl)acrylate, and butyl 3-anilino-2-(2,4,5-trifluoro-3-methyl-6-nitrobenzoyl)acrylate.

Examples of the benzoylacrylic acid derivative (formula 3) wherein $R^2$ is an alkylamino group:

methyl 3-(N'-methylhydrazino)-2-(2,4,5-trifluoro-3-methyl-6-nitrobenzoyl)acrylate, ethyl 3-(N'-methylhydrazino)-2-(2,4,5-trifluoro-3-methyl-6-nitrobenzoyl)acrylate, propyl 3-(N'-methylhydrazino)-2-(2,4,5-trifluoro-3-methyl-6-nitrobenzoyl)acrylate, butyl 3-(N'-methylhydrazino)-2-(2,4,5-trifluoro-3-methyl-6-nitrobenzoyl)acrylate, methyl 3-(N'-ethylhydrazino)-2-(2,4,5-trifluoro-3-methyl-6-nitrobenzoyl)acrylate, ethyl 3-(N'-ethylhydrazino)-2-(2,4,5-trifluoro-3-methyl-6-nitrobenzoyl)acrylate, propyl 3-(N'-ethylhydrazino)-2-(2,4,5-trifluoro-3-methyl-6-nitrobenzoyl)acrylate, butyl 3-(N'-ethylhydrazino)-2-(2,4,5-trifluoro-3-methyl-6-nitrobenzoyl)acrylate, methyl 3-(N'-propylhydrazino)-2-(2,4,5-trifluoro-3-methyl-6-nitrobenzoyl)acrylate, ethyl 3-(N'-propylhydrazino)-2-(2,4,5-trifluoro-3-methyl-6-nitrobenzoyl)acrylate, propyl 3-(N'-propylhydrazino)-2-(2,4,5-trifluoro-3-methyl-6-nitrobenzoyl)acrylate, butyl 3-(N'-propylhydrazino)-2-(2,4,5-trifluoro-3-methyl-6-nitrobenzoyl)acrylate, methyl 3-(N'-butylhydrazino)-2-(2,4,5-trifluoro-3-methyl-6-nitrobenzoyl)acrylate, ethyl 3-(N'-butylhydrazino)-2-(2,4,5-trifluoro-3-methyl-6-nitrobenzoyl)acrylate, propyl 3-(N'-butylhydrazino)-2-(2,4,5-trifluoro-3-methyl-6-nitrobenzoyl)acrylate, butyl 3-(N'-butylhydrazino)-2-(2,4,5-trifluoro-3-methyl-6-nitrobenzoyl)acrylate, methyl 3-(N'-tert-butylhydrazino)-2-(2,4,5-trifluoro-3-methyl-6-nitrobenzoyl)acrylate, ethyl 3-(N'-tert-butylhydrazino)-2-(2,4,5-trifluoro-3-methyl-6-nitrobenzoyl)acrylate, propyl 3-(N'-tert-butylhydrazino)-2-(2,4,5-trifluoro-3-methyl-6-nitrobenzoyl)acrylate, and butyl 3-(N'-tert-butylhydrazino)-$^2$-(2,4,5-trifluoro-3-methyl-6-nitrobenzoyl)acrylate.

Examples of the benzoylacrylic acid derivative (formula 3) wherein $R^2$ is a dialkylamino group:

methyl 3-(N',N'-dimethylhydrazino)-2-(2,4,5-trifluoro-3-methyl-6-nitrobenzoyl)acrylate, ethyl 3-(N',N'-dimethylhydrazino)-2-(2,4,5-trifluoro-3-methyl-6-nitrobenzoyl)acrylate, propyl 3-(N',N'-dimethylhydrazino)-2-(2,4,5-trifluoro-3-methyl-6-nitrobenzoyl)acrylate, butyl 3-(N',N'-dimethylhydrazino)-2-(2,4,5-trifluoro-3-methyl-6-nitrobenzoyl)acrylate, methyl 3-(N',N'-diethylhydrazino)-2-(2,4,5-trifluoro-3-methyl-6-nitrobenzoyl)acrylate, ethyl 3-(N',N'-diethylhydrazino)-2-(2,4,5-trifluoro-3-methyl-6-nitrobenzoyl)acrylate, propyl 3-(N',N'-diethylhydrazino)-2-(2,4,5-trifluoro-3-methyl-6-nitrobenzoyl)acrylate, butyl 3-(N',N'-diethylhydrazino)-2-(2,4,5-trifluoro-3-methyl-6-nitrobenzoyl)acrylate, methyl 3-(N',N'-dipropylhydrazino)-2-(2,4,5-trifluoro-3-methyl-6-nitrobenzoyl)acrylate, ethyl 3-(N',N'-dipropylhydrazino)-2-(2,4,5-trifluoro-3-methyl-6-nitrobenzoyl)acrylate, propyl 3-(N',N'-dipropylhydrazino)-2-(2,4,5-trifluoro-3-methyl-6-nitrobenzoyl)acrylate, butyl 3-(N',N'-dipropylhydrazino)-2-(2,4,5-trifluoro-3-methyl-6-nitrobenzoyl)acrylate, methyl 3-(N',N'-dibutylhydrazino)-2-(2,4,5-trifluoro-3-methyl-6-nitrobenzoyl)acrylate, ethyl 3-(N',N'-dibutylhydrazino)-2-(2,4,5-trifluoro-3-methyl-6-nitrobenzoyl)acrylate, propyl 3-(N',N'-dibutylhydrazino)-2-(2,4,5-trifluoro-3-methyl-6-nitrobenzoyl)acrylate, and butyl 3-(N',N'-dibutylhydrazino)-2-(2,4,5-trifluoro-3-methyl-6-nitrobenzoyl)acrylate.

The reaction temperature for reaction step-2 is preferably lower than 10° C. A temperature which is −10° C. or above and is lower than +10° C., particularly from 0 to 5° C., is particularly preferred. A reaction temperature of 10° C. or above unfavorably increases the by-product and thereby decreases the yield. It is preferred to keep the reaction product lower than 10° C., because heating after completion of the reaction can lead to increase of the by-product.

It is preferred to carry out reaction step-2 in the presence of a reaction solvent. As the reaction solvent, a reaction solvent which allows precipitation of the benzoylacrylic acid derivative (formula 3) or a reaction solvent which allows precipitation of the benzoylacrylic acid derivative (formula 3) on addition of water after completion of the reaction is preferred. As the reaction solvent, methanol or ethanol may be mentioned. The amount of the reaction solvent is preferably from 0.5 to 100 times as much by weight as the amount of the aminoacrylic acid derivative (formula 1).

Further, it is preferred to carry out the reaction in the absence of an acid. The reaction can give a high yield of a compound represented by formula 3 even in the absence of an acid.

The bonzoylacrylic acid derivative (formula 3) is useful as an intermediate for production of quinolone compounds having an amino group or a nitro group at the 5-position, a fluorine atom at the 6-position and a methyl group at the 8-position on the quinolone nucleus and convertible to the quinolone compound represented by the previously mentioned formula 4 which is useful as a synthetic antibacterial agent by the process disclosed in JP-A-8-198819.

Now, the present invention will be described by referring to Examples. However, the present invention is by no means restricted to such specific Examples. High performance liquid chromatography (HPLC) was done under the following conditions.

Detector: UV (240 nm)

Column: TSK-gel ODS-80TM

Column Temp.: 30° C.

Mobile phase: (acetonitrile)/(pH 7.0 phosphate buffer)= 1/1

Flow rate: 1.0 ml/min

EXAMPLE 1

Preparation of ethyl 3-dimethylamino-2-(2,4,5-trifluoro-3-methyl-6-nitrobenzoyl)acrylate 1.4 g (0.01 mol) of ethyl 3-dimethylaminoacrylate, 15 mg of ethyl acetate and 0.8 mg (0.01 mol) of pyridine were loaded and cooled below 5° C., and a liquid mixture of 3 g (0.01 mol) of 2,4,5-trifluoro-3-methyl-6-nitrobenzoyl chloride and 5 ml of ethyl acetate was added dropwise while the temperature was maintained at 0 to 5° C. The resulting mixture was stirred at 5° C. for 1 hour and then stirred at room temperature (25° C.) overnight (12 hours). The precipitated pyridine hydrochloride was filtered off, and the filtrate was concentrated under reduced pressure to give 3.62 g of ethyl 3-dimethylamino-2-(2,4,5-trifluoro-3-methyl-6-nitrobenzoyl)acrylate with a 87% purity (in terms of the percentage of the peak area in HPLC) as the residue.

For preparation of a sample for spectrometry, 3.6 g of the residue was purified by silica gel column chromatography (eluent: toluene:acetonitrile=10:1 (volume ratio) to give 1.7 g of a brown oily substance. The purity of ethyl 3-dimethylamino-2-(2,4,5-trifluoro-3-methyl-6-nitrobenzoyl)acrylate purity in the form of the brown oily substance was 97% (in terms of the percentage of the peak area in HPLC).

$^1$H-NMR (CDCl$_3$) δ: 1.06 (3H, t, J=7.2 Hz), 2.28 (s, 3H), 3.10 (3H, brs), 3.39 (3H, brs), 4.02 (2H, q, J=7.2 Hz), 8.00 (1H, s).

IR (KBr) cm$^1$: 1695, 1635, 1555, 1381, 1097.

EXAMPLE 2

Preparation of ethyl 3-dimethylamino-2-(2,4,5-trifluoro-3-methyl-6-nitrobenzoyl)acrylate 1.4 g (0.01 mol) of ethyl 3-dimethylaminoacrylate, 15 ml of ethyl acetate and 1.4 ml (0.01 mol) of triethylamine were loaded and cooled to 5° C., and a liquid mixture of 3.5 g (0.011 mol) of 2,4,5-trifluoro-3-methyl-6-nitrobenzoyl chloride and 5 ml of ethyl acetate was added dropwise while the temperature was maintained at 0 to 5° C. The resulting mixture was stirred at 5° C. for 1 hour and then stirred at room temperature (25° C.) for 2 hours. The precipitated triethylamine hydrochloride was filtered off, and the filtrate was concentrated under reduced pressure to give ethyl 3-dimethylamino-2-(2,4,5-trifluoro-3-methyl-6-nitrobenzoyl)acrylate with a 43.6% purity as the residue.

EXAMPLE 3

Preparation of ethyl 3-cyclopropylamino-2-(2,4,5-trifluoro-3-methyl-6-nitrobenzoyl)acrylate 14.4 g (0.1 mol) of ethyl 3-dimethylaminoacrylate, 60 ml of ethyl acetate and 8.0 ml (0.1 mol) of pyridine were loaded and cooled to 5° C., and a liquid mixture of 27.8 g (0.1 mol) of 2,4,5-trifluoro-3-methyl-6-nitrobenzoyl chloride and 15 ml of ethyl acetate was added dropwise while the temperature was maintained at 0 to 5° C. The resulting mixture was stirred at 5° C. for 1 hour and then stirred at room temperature (25° C.) overnight (12 hours). The precipitated pyridine hydrochloride was filtered off, and the filtrate was concentrated under reduced pressure.

The residue was cooled to 0° C. with 50 ml of ethanol, and 6.1 g (0.11 mol) of cyclopropylamine in 10 ml of ethanol was added dropwise while the temperature was maintained at 0 to 5° C. After 1 hour of stirring, 50 ml of water was added, and the precipitated crystals were collected by filtration and flushed with 5 mg of ethanol. The crystals weighed 35.2 g in a wet state. The crystals were dried to give 29.2 g of ethyl 3-cyclopropylamino-2-(2,4,5-trifluoro-3-methyl-6-nitrobenzoyl)acrylate. The yield was 78.4%, and the purity in terms of the percentage of the peak area was 98.5%.

INDUSTRIAL APPLICABILITY

The process of the present invention makes it possible to produce an aminoacrylic acid derivative (formula 1) and a benzoylacrylic acid derivative (formula 3) useful as an intermediate and precursor of medicinal drugs in a high yield through a small number of steps.

What is claimed is:

1. An aminoacrylic compound having the formula (1):

wherein $R^1$ is a lower alkyl.

2. The aminoacrylic compound of claim 1, wherein $R^1$ is $C_1$–$C_4$ alkyl.

3. The aminoacrylic compound of claim 2, wherein $R^1$ is methyl.

4. The aminoacrylic compound of claim 2, wherein $R^1$ is ethyl.

5. The compound of claim 2, wherein $R^1$ is $C_3$-alkyl.

6. The compound of claim 2, wherein $R^1$ is $C_4$-alkyl.

7. The compound of claim 2, wherein $R^1$ is not $C_1$–$C_4$ alkyl.

* * * * *